United States Patent [19]
Blouir

[11] Patent Number: 5,220,592
[45] Date of Patent: Jun. 15, 1993

[54] DIAGNOSTIC IMAGING SYSTEM WITH COMPACT MULTI-FUNCTION CONTROLLER

[75] Inventor: Charles D. Blouir, Chagrin Falls, Ohio

[73] Assignee: Picker International, Inc., Highland Heights, Ohio

[21] Appl. No.: 880,567

[22] Filed: May 8, 1992

[51] Int. Cl.$^5$ .............................. H05G 1/58
[52] U.S. Cl. .................... 378/114; 378/116; 341/20
[58] Field of Search ............... 378/114, 115, 116, 91, 378/95, 195-198, 204; 341/20, 21, 22, 27

[56] References Cited

U.S. PATENT DOCUMENTS

| | | | |
|---|---|---|---|
| 4,200,798 | 4/1980 | Nevendorf et al. | 378/116 |
| 4,246,452 | 1/1981 | Chandler | 341/20 |
| 4,469,330 | 9/1984 | Asher | 341/22 |
| 4,516,939 | 5/1985 | Crimmins, Jr. | 341/22 |
| 4,553,254 | 11/1985 | Bach et al. | 378/116 |
| 5,020,089 | 5/1991 | Cramer et al. | 378/198 |
| 5,159,623 | 10/1992 | Niepel et al. | 378/196 |

Primary Examiner—David P. Porta
Attorney, Agent, or Firm—Timothy B. Gurin

[57] ABSTRACT

A diagnostic imaging system is comprised of a plurality of linearly adjustable functions and a plurality of binary selectable functions which are controlled by a multi-function joystick controller. The controller has a plurality of function select switches, a joystick, a mushroom cap rotatably engaged on the joystick, a microprocessor, a plurality of switches individually engageable by pivoting the joystick and a pair of switches individually engageable by clockwise or counterclockwise rotation of the mushroom cap. The switches and the microprocessor cooperate such that the selection of a first function select switches causes the operation of the joystick switches and/or mushroom cap switches to be linked to a predetermined first set of imaging system functions. Subsequently, when a second function select switches is selected the joystick switches and mushroom cap switches thereafter operate a predetermined second set of imaging system functions until another function select switch is selected.

15 Claims, 3 Drawing Sheets

DIAGNOSTIC IMAGING SYSTEM WITH COMPACT MULTI-FUNCTION CONTROLLER

BACKGROUND OF THE INVENTION

The present invention relates to radiographic imaging in medical diagnostic equipment. It finds particular application in conjunction with vascular imaging systems and will be described with reference thereto however, it should be appreciated that the invention may also find application in conjunction with other equipment where a compact controller for select adjustable positioning of various system components is desired.

A typical vascular imaging system includes a gantry, a patient table, a source of x-radiation and a radiographic receptor. The gantry supports the source and receptor such that a radiation beam produced by the source is propagated along a path to the radiation receptor. The patient table is disposed in the path between the source and receptor. The gantry typically has one or more drive means which provide for controlled clockwise (CW) or counterclockwise (CCW) rotation of the source-receptor about a horizontal axis and separate CW or CCW rotation of the source-receptor about a vertical axis. The rotation of the source-receptor combination permits the portion of the patient under examination to be inspected from a variety of different selectable views. The patient table typically includes a drive means for variable, up-down, adjustment of the table height. The imaging system may also have a separate drive means for variable adjustment of the source to receptor distance for accommodating the table and patients of different size therebetween. The imaging system may also have a separate drive means for variable adjustment of shutters and irises, the adjustment providing for regulated control of the opening or closing of the shutters or irises for regulating the beam propagation path. Lastly, the imaging system may have one or more drive means for selectively moving and/or rotating one or more of a plurality of filters, disposed between the source and the patient table, for selectively filtering the x-radiation propagating from the source such that of appropriate radiation energy is received by the receptor.

In addition to drive means for regulated adjustment of certain linear functions the imaging system typically has one or more binary selectable functions where two or more states of said functions are chosen by the sequential engagement of the same function switch. One such binary function is a receptor magnification mode which selectively views a subset of the beam received at the receptor and displays said subset as a full view on a viewing means, such as a television screen. Still another binary function is a field light for providing a visual indication of where the beam path will enter the patient, said field light typically used to align the gantry. Lastly, some imaging systems may include a second source-receptor combination disposed about the patient for providing alternate selectable views of the same portion of the patient without having to reposition the first source-receptor combination.

At least one single pole single throw (SPST) switch is wired to each imaging system function. For drive means two (2) SPST switches or one (1) single pole double throw (SPDT) switch, is wired to each drive means to control the CW or CCW rotation of the select drive means. All of the switches are installed in a common control panel. Because each imaging system function is wired to and controlled by an individual switch the control panel tends to be relatively large and complex. It should also be appreciated that a wiring harness connecting the switches to their respective imaging system function tends to be relatively bulky because of the number of wires required to connect the controller to the imaging system.

A first attempt to overcome the objectionable size and complexity associated with a control panel having individual switches controlling the separate imaging system functions resulted in a plurality of individually engageable switches each having a common engagement means. One such arrangement includes a pivotal joystick having four (4) momentary contact switches disposed thereabout such that any one of said switches can be individually engaged by the pivotal movement of the joystick. A joystick-switch combination was provided for each of the separate functions to be controlled. One benefit of using the joystick-switch combination is that one such combination replaces two to four separate switches in the control panel with a corresponding reduction in the size and complexity of the panel. Another benefit of having the above joystick-switch combination is that the combination provides the occasion to logically associate imaging system functions. For example, rotational positioning of the source-receptor about the horizontal axis may be controlled by operation of a first joystick in the $\pm y$ direction while rotational positioning of the source-receptor about a vertical axis may be linked to operation of the first joystick in the $\pm x$ direction. It should be recognized that the number of joystick-switch combinations required is related to the number of different imaging system functions to be controlled thereby. The joystick-switch combination results in a smaller and less involved control panel than would be required if individual switches were disposed in the control panel face. The large number of joystick-switch combinations results however, in a control panel that is still relatively large and involved. Also, since each switch is still wired directly to the function it controls the number of actual switches has not decreased and the number of connecting wires remains the same as above.

For patient safety it is typically desirable to only engage one imaging system function at a time particularly those functions involving movement of the patient, the gantry or the receptor while the patient is dispose on the table.

In the above two embodiments the control panel is typically mounted to a floor rollable cart for rollable positioning thereof. The size of the panel and the wiring harness make the control panel difficult to move around the room for viewing the positioning of the imaging system or to move the panel and cable clear of the imaging system during imaging operation.

The present invention contemplates an improved control panel which integrates the functions of the above describe control panels into a compact, portable package that has a minimal number of switches and joysticks associated therewith.

SUMMARY OF THE INVENTION

Disadvantages of the prior art are reduced or overcome by use of an integrated control panel having a plurality of function select switches, a single joystick and a microprocessor in a compact arrangement. The joystick has a plurality of momentary contact switches disposed at one end for select engagement by pivotal movement of the joystick. The joystick also has a mushroom cap rotatably engaged on the other end for rotatably engaging a pair of momentary contact switches by the respective CW and CCW rotation of the cap. Two or more of the function select switches cooperate with the microprocessor, the joystick switches and/or the mushroom cap switches such that the selection of one of said function select switches links joystick switches and/or the mushroom cap switches to the control of select imaging system functions.

An advantage of the present invention is that one joystick-switch combination, a plurality of function select switches and a microprocessor replace a plurality of individually wired joystick-switch combinations or a plurality of individual switches.

Another advantage of the present invention is that it can be hand held.

Another advantage of the present invention is its reduced user complexity.

Still another advantage of the present invention is the reduced size of the wiring harness between the control panel and the imaging system.

BRIEF DESCRIPTION OF THE DRAWINGS

The invention may take form in various parts, arrangements of parts or sizes of parts. the drawings are only for the purpose of illustrating the preferred embodiment and are not to be construed a limiting the invention.

DETAILED DESCRIPTION OF THE PREFERRED EMBODIMENT

Figure 1:
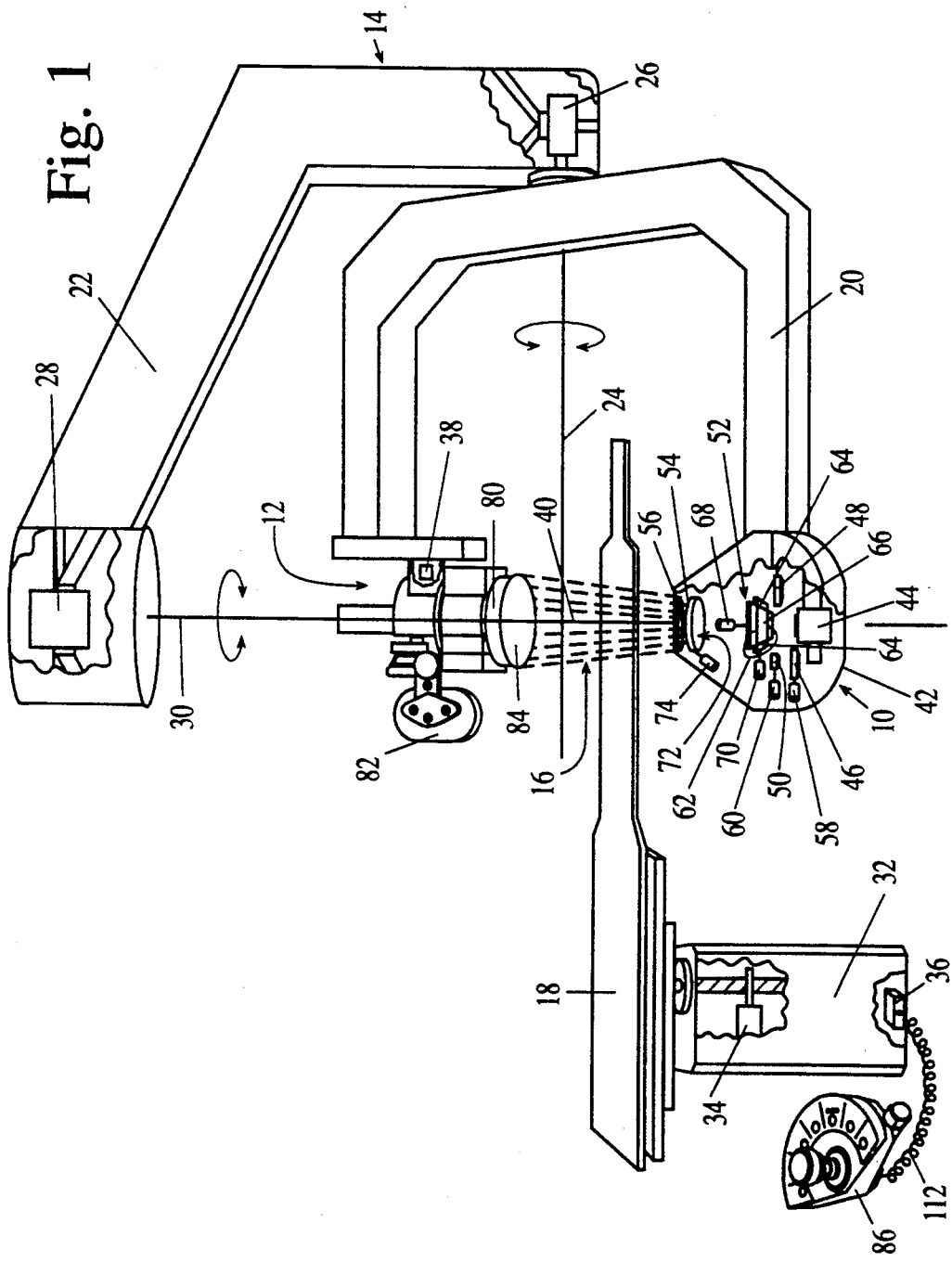
FIG. 1 is a perspective view of an exemplary imaging system where the invention is used.
Figure 2:
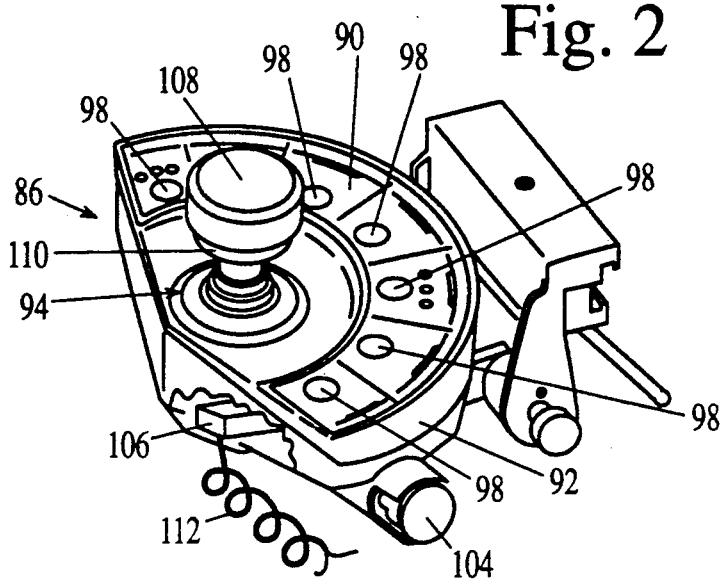
FIG. 2 is a perspective view of the multi-function joystick controller.
Figure 3:
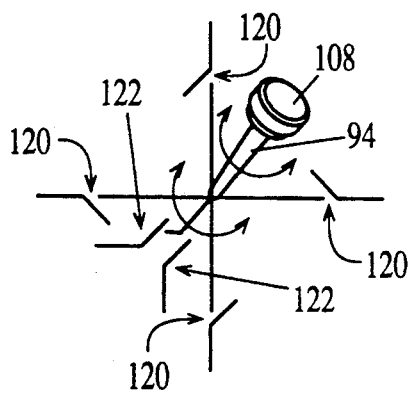
FIG. 3 is a schematic view of the joystick, the joystick switches and the cap switches.
Figure 4:
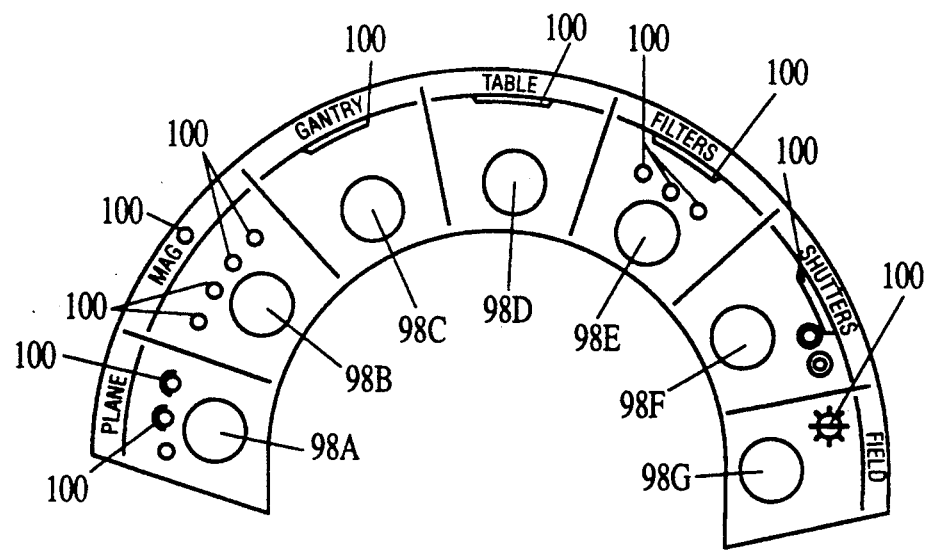
FIG. 4 is a plan view of a portion of controller showing the function control switches in isolation.
Figure 5:
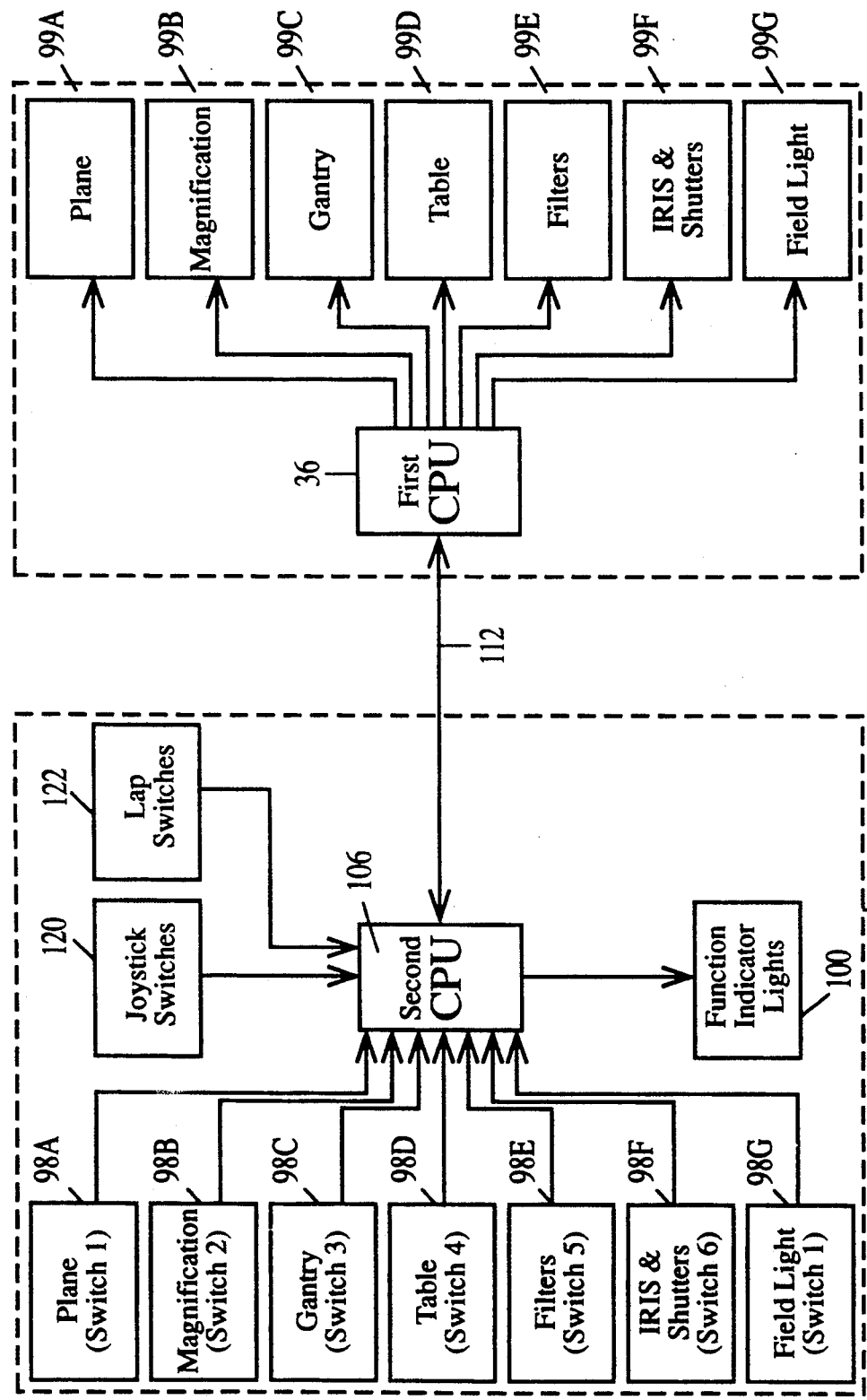
FIG. 5 is block diagram of the of the multi-function joystick controller.

With reference to FIG. 1, an x-radiation source 10 and x-radiation receptor 12 are supported on a position adjustable gantry 14 such that a diverging beam of radiation 16 propagating from the source is received by the receptor. A patient table 18 is disposed in the beam path for receiving a patient under examination thereon. The gantry has a U arm 20 rotatably mounted to an L arm 22 for rotation about horizontal axis 24. The U arm is coupled to a U arm drive means 26 which can rotate the U arm clockwise (CW) or counterclockwise (CCW) about the horizontal axis. The L arm is coupled to an L arm drive means 28 which rotates the L arm CW or CCW about a vertical axis 30. The patient table includes a base 32 for supporting the patient table 18 and a table drive means 34 coupled to the patient table for vertical height adjustment thereof. The patient table has a first microprocessor 36 contained therein which will be described in detail later. The receptor 12 includes a receptor drive means 38 for adjusting the distance between the source and the receptor along an axis 40, defined by the central portion of the beam path between the source and receptor. It should be appreciated that the U arm can be horizontally rotated about axis 24 such that the beam path axis 40 does not coincide with the gantry vertical axis 30.

The source 10 is comprised of a housing 42 including an x-ray generator 44, a pair of selectable collimator filters (46,48), a leg filter 50, an adjustable shutter assembly 52, an iris 54 and a field light 56. The collimator and leg filters selectively filter x-radiation rays emanating from the source that do not contribute to the imaging operation, each filter providing a different measure of filtration. The filters can be selectively urged into the beam path by a first filter drive means 58, a second filter drive means (not shown) or a third filter drive means 60. The shutter assembly is comprised of a first pair of opposite partitions 62 and a second pair of opposite partitions 64 defining a rectangular aperture 66 through which the x-radiation rays pass through. The first and second pair of partitions are selectively positionable by a first and second partition drive means (68, 70) respectively. The iris 54 is comprised of a plurality of overlapping partitions (not shown) cooperating to define a variable diameter circular aperture 72 through which the x-radiation rays pass through thereby defining the final x-radiation beam dimension. The diameter of the iris aperture is adjusted by a drive means 74 adjusting the iris partitions. The field light 56 is switchably engaged for visualizing the beam path direction.

The receptor 12 is comprised of a container 78 having an image intensifier tube 80, a video camera 82, and a drive means 38 for varying the distance between the source and receptor. The intensifier tube has an input 84 for receiving the radiation from the source and an output which produces a visual light indication of the radiographic image received at the input screen. The video camera is positioned to view the output and communicate said output to a viewing means, such as a television. The receptor has at least one magnification means which views less than the full diameter of the of the input screen and displays said view on the viewing means.

An alternate imaging system embodiment would further include a second source-receptor combination secured to a second U arm at a right angle to the first U arm. The second source-receptor combination providing separate views of the patient in different planes without having to move the source-receptor combinations to a different position.

With reference to FIGS. 2, 3, 4 and 5 and continuing reference to FIG. 1, a multi-function controller 86 is provided. The multi-function controller includes a face 90, a body 92, a joystick 94 disposed in the face, a plurality of function select switches (98A through 98G) individually labeled to indicate which imaging system function (99A through 99G) is selectable by each switch and having associated indicator lights 100 arranged in an arc around the joystick, an emergency stop switch 104 and a second microprocessor 106. One end of the joystick shaft is pivotally biased in the face 90 such that the joystick tends to remain generally perpendicular to the face when the joystick is at rest. The other end of the joystick shaft has a rotatable mushroom cap 108 attached thereto for CW or CCW rotation of the cap relative to the face. The joystick includes a locking means (not shown) for securing the joystick against unintended pivotal motion and preventing unintended rotational motion of the mushroom cap. The joystick has a enabling ring 110 movably biased between the face 90 and the mushroom cap 108 and operably connected to the joystick locking means such that when the ring is urged against the bias the joystick locking means is released thereby allowing pivoting of the joystick or rotation of the mushroom cap. The joystick has a plurality of momentary contact switches 120 secured adjacent the pivoting end (hereinafter "joystick switches") such that the joystick can pivotally engage each joystick switch exclusive of the remaining joystick switches. The multi-function controller also includes a pair of momentary contact switches 122 engageable by the respective clockwise (CW) and counterclockwise (CCW) rotation of the mushroom cap (hereinafter "cap switches").

The second microprocessor 106 is electrically connected to the switches, the function indicator lights and a cable means 112. The cable means electrically connects the second microprocessor to the first microprocessor 36. The second microprocessor monitors the contact status of the function select switches, joystick switches and the cap switches. When a specific function select switch is selected the second microprocessor associates the operation of the joystick and/or cap switches to the select set of system functions. Thereafter, the second microprocessor transmits a uniquely coded control signals to the first microprocessor in response to the select engagement of the joystick and-/or cap switches. The first microprocessor accepts the unique code and converts said code into a control signal for operating a select imaging system function in known manner.

More specifically, two (2) or more function select switches cooperate with the second microprocessor such that the selection of a first function select switch results in the operation of the joystick and cap switches to be associated with a first set of imaging system functions; said imaging system functions selected by the engagement of the first function select switch. When a second function select switch is selected the operations associated with the first set of imaging system functions is replaced with the operations of a second set of imaging system functions; said second set of imaging system functions selected by the engagement of the second function select switch.

For example, the momentary engagement of the function select switch labeled "GANTRY" 98 uniquely links the engagement of the joystick and cap switches to movements of the gantry arms and adjustment of the distance between the source and receptor. Specifically, the U arm drive means 26 drives the U arm CW or CCW in response to the respective engagement of one of a first pair of joystick switches, the drive means 38 causes the receptor to move closer to or further from the source in response to the respective engagement of one of a second pair of joystick switches and the L arm drive means 30 drives the L arm CW or CCW in response to the respective engagement of one of the cap switches.

If, while the "GANTRY" functions are linked to the joystick and cap switches, the function select switch labeled "TABLE" 98 is engaged the joystick and cap switch operations associated with the "GANTRY" Function Control Switch are replaced with the operations associated with the "TABLE" Function Control Switch. Specifically, the vertical motion of the patient table is now controlled in response to the respective engagement of one pair of joystick switches. Since the Function Control Switch labeled "TABLE" only controls the up and down vertical motion of the table only one pair of joystick switches are required therefore, the remaining joystick and cap switches are disabled.

It should be appreciated that the selection of designated function select switches causes the joystick, the joystick switches and the cap switches combination to selectively control a different set of imaging system functions without having a relatively large number of individual switches and/or individually wired joystick-switch combinations connected to each function. It should also be appreciated that some of the function select switches may control separate imaging system functions without linking the operation of the joystick and its associated switches thereto. Also, some function select switches link the operation of the joystick and its associated switches to a specific set of imaging system functions such that each successive engagement of the same function select switch causes the operation controlled by the joystick and its associated switches to be replaced with other imaging system functions.

The multi-function controller 86 has a plurality of function select switches (98A through 98G), joystick switches 120, cap switches 122 and a second microprocessor 114. The switches of the controller are inputs to the second microprocessor. Communication between the first microprocessor 36 and the second microprocessor 106 occurs through cable means 112. The second microprocessor transmits a unique code to the first microprocessor in response to the select engagement of various function select switches, joystick switches and-/or cap switches. Additionally, the second microprocessor illuminates one or more associated function indicator light(s) 100 in response to the engagement of an associated function select switch. When more than one set of functions are associated with a single function select switch the sequential engagement of the same switch causes the various functions to be individually linked to the joystick switches and/or cap switches in a predetermined sequence. The first microprocessor 36 receives the unique code and converts said code into signals which control the operation of the various functions (99A through 99G) associated with the selection of the respective function select switches (98A through 98G) and the subsequent engagement of the joystick switches and/or cap switches.

The above invention has been described with reference to the preferred embodiments. Obvious modifications, combinations of functions and alterations will occur to other upon reading the preceding detailed description. It is intended that the invention be construed as including all such modifications and alterations insofar as they come within the scope of the appended claims or the equivalents hereof.

Having described the preferred embodiment the invention is now claimed to be:

1. An x-ray imaging system, comprising;
   a source of x-radiation for propagating a beam of radiation along a path;
   a beam receptor means for receiving the beam and converting the received radiation into a visible image;
   a movable gantry means for functionally holding the source and the receptor in movable relative position, the movable gantry having a gantry drive means for effecting gantry movement;
   a movable support means functionally positioned between the source and receptor for selectively locating a supported subject under examination between the source and detector, the movable support having a support drive means for effecting support means movement;

a multi-function control means, comprising;
  a plurality of function select switches for dedicated selection of a predetermined function;
  a singular positional control means for selectively controlling the operation of at least one drive means when a corresponding function select switch is activated.

2. The imaging system as set forth in claim 1 further including a third drive means for moving the source and receptor with respect to each other along an axis therebetween.

3. The imaging system as set forth in claim further including an adjustable iris disposed between the source and the support means for limiting the beam path, the adjustable iris having a forth drive means for effecting adjustment of the iris aperture.

4. The imaging system as set forth in claim 1 further including an adjustable shutter disposed between the source and the support means for limiting the beam path, the adjustable shutter having a fifth drive means for effecting adjustment of the shutter aperture.

5. A multi-function controller comprising:
  an enclosure having a power switch, an emergency stop switch, at least two function select switches, a joystick and a communication means integrated therein;
  the function switches, joystick and communication means electrically interconnected such that one or more predetermined function switches cooperate with the communications means to link the joystick to the communication means when any one of said switches are engaged, the other function switches providing direct binary switching to the communication means;
  a means for ensuring that the engagement of one joystick function select switch is mutually exclusively of the engagement of other joystick function select switches;
  the communication means operatively connected to recognize which joystick function select switch is engaged and what other direct switching switches are engaged;
  the communication means including means for uniquely encoding each function switch or interconnected joystick movement thereof with a unique code and for communicating said code to a receiving means; and
  the receiving means having a means for receiving and decoding the unique code from the communication means and for converting said decoded information into stimulus for engaging a select function corresponding to predetermined function in response to each function switch selected.

6. The joystick as set forth in claim 5 further including a biased enabling ring movably engaged between a top and bottom of the joystick for releasing the joystick from a home position when the enabling ring is moved against the biasing means.

7. A radiographic imaging system comprising;
  a gantry, a patient table, a source of radiographic energy including an x-ray source enclosed in a container, a radiographic receptor including an image intensifier tube having an input face and an output face, a video camera having an input and an output, a closed circuit television and a multi-function joystick controller;
  the gantry having a first arm and a second arm; the first arm having a symmetrical shape defining a gap at the ends thereof, the second arm having at least a generally horizontal portion at one end and a generally vertical portion at the other end, the first arm rotatably engaged to the vertical portion of the second arm such that the ends of first arm are symmetrically disposed on either side of a horizontal axis passing adjacent the first arm's iso center, the horizontal end of the second arm rotatably engaged to a horizontal structure such that the second arm rotates about a vertical axis passing adjacent the first arms iso center;
  the gantry further including a gantry drive means for selectively rotating the first arm or the second arm about their respective rotational axis in response to a drive stimulus;
  the x-ray source and image intensifier tube disposed on either end of the first arm defining a gap therebetween for receiving an object to be imaged, such as a human patient, disposed on the patient table, the x-ray source output and image intensifier input face aligned such that radiation propagating from the x-ray source passes through the object to be imaged and onto the input face of the intensifier tube, the intensifier tube converting radiographic information received on the input face thereof into a relatively bright visible light image on the intensifier tube output face;
  the patient table having a upper surface for receiving a patient thereon, the table further including a table drive means for selectively adjusting the vertical position of the table in response to a drive stimulus;
  the video camera input fixedly secured adjacent the intensifier tube output face such that the camera input views the intensifier output face, the output of the camera connected to the television such that the image viewed by the camera is displayed on the television;
  the multi-function joystick controller comprising;
    a housing having a power switch, an emergency stop switch, a joystick, a communication means and at least two joystick function switches integrated therein,
    the joystick function switches linking the joystick to the communication means when engaged;
    a means for ensuring that the engagement of one joystick function switch is mutually exclusively of the engagement of other joystick function switches;
    the joystick comprising;
      an arm having a variable position pivot engaged in the housing;
      a means for recognizing the direction and extent of pivotal motion of the arm from a home position; and
      a rotatable switch for engaging a set of contacts when the joystick is rotated clockwise about its longitudinal axis and which engages a second set of contacts when the joystick is rotated counter clockwise about its longitudinal axis;
  the communication means including means for recognizing which joystick function switch is engaged and for uniquely encoding the pivotal or rotational movement of the joystick with a unique code indicative of said motion in response to the function switch selected, the communication means conveying said unique codes to a receiving means; and the receiving means having means for receiving and converting said coded information into stimulus for selectively engaging the gantry drive means or the table drive means in response to pivotal or rotational motion of the joystick for a selected joystick function switch.

8. The joystick as set forth in claim 7 further including a biased enabling ring movably engaged between a top and bottom of the joystick for releasing the joystick from a home position when the enabling ring is moved against the biasing means.

9. The apparatus as set forth in claim 8 further including;
   a gap drive means for varying the gap distance between the x-ray source and the intensifier input face;
   the gap drive means cooperating with the receiving means, the communication means, at least one joystick function switch and the joystick such that the selection of the select joystick function switch links the pivoting and rotational motions of the joystick to the communication means, the communications means conveying a unique code to the receiving means in response to one of a select pivotal and rotational motions of the joystick, the receiving means receiving said unique code and conveying a stimulus to the gap drive means in response thereto such that the gap distance diminishes for one of a select pivotal or rotational movement of the joystick in one direction and the gap distance increases in response to movement of the joystick in an opposite direction.

10. The apparatus as set forth in claim 8 further including;
    an adjustable iris, disposed between the x-ray source and the intensifier input face, for adjustably controlling an aperture through which the radiation from the x-ray source will propagate, the iris having a drive means associated therewith for controlling the opening of the iris in response to a stimulus;
    the iris drive means cooperating with the receiving means, the communication means, at least one joystick function switch and the joystick such that the selection of a select joystick function switch links the pivoting and rotational motions of the joystick to the communication means, the communications means conveying a unique code to the receiving means in response to a select pivotal or rotational motion of the joystick, the receiving means receiving said unique code and conveying the iris drive means stimulus to the iris drive means in response thereto.

11. The apparatus as set forth in claim 8 further including;
    an adjustable shutter, disposed between the x-ray source and the intensifier input face, for adjustably controlling an aperture through which the radiation from the x-ray source will propagate, the shutter having a drive means associated therewith for selectively controlling the opening of the shutter in response to a stimulus;
    the shutter drive means cooperating with the receiving means, the communication means, at least one joystick function switch and the joystick such that the selection of a select joystick function switch links the pivoting and rotational motions of the joystick to the communication means, the communications means conveying a unique code to the receiving means in response to a select pivotal or rotational motion of the joystick, the receiving means receiving said unique code and conveying the shutter drive means stimulus to the shutter drive means in response thereto.

12. The apparatus as set forth in claim 8 wherein the multi-function joystick controller further includes at least one binary function switch integrated therein.

13. The apparatus as set forth in claim 12 further including;
    a visible light source enclosed within the x-ray source container for visual adjustable positioning of the x-ray source;
    the visible light source cooperating with the receiving means, the communication means and the binary function switch such that the selection of the function switch is recognized by the communications means, the communication means conveys a unique code to the receiving means in response to the engagement of said function switch, the receiving means receives the unique code and conveys a stimulus to the light source which changes the state of the light source in response thereto.

14. The apparatus as set forth in claim 12 further including;
    at least one selectively engageable radiation filter disposed between the x-ray source and the intensifier input screen for filtering the radiation propagating from the x-ray source, the filter having a drive means associated therewith for selectively engaging the filter;
    the filter drive means cooperating with the receiving means, the communication means and the binary function switch such that the selection of the function switch is recognized by the communications means, the communication means conveys a unique code to the receiving means in response to the engagement of said function switch, the receiving means receives the unique code and conveys a stimulus to the filter drive means which changes the engagement state of the filter in response thereto.

15. The apparatus as set forth in claim 12 further including;
    a magnification means associated with the intensifier tube for selectively isolating at least one portion of the intensifier input face such that when the magnification means is engaged the radiographic information contained on select portion is converted to a visual light image on the intensifier output face, the magnification means having a selection means for selectively engaging the magnification means;
    the selection means cooperating with the receiving means, the communication means and the binary function switch such that the selection of the function switch is recognized by the communications means, the communication means conveys a unique code to the receiving means in response to the engagement of said function switch, the receiving means receives the unique code and conveys a stimulus to the selection means which changes the engagement state of the magnification means in response thereto.

* * * * *